United States Patent
Tan et al.

(10) Patent No.: US 6,734,697 B1
(45) Date of Patent: May 11, 2004

(54) DIE LOCATION ON UNGROUNDED WAFER FOR BACK-SIDE EMISSION MICROSCOPY

(75) Inventors: Kevan Tan, San Jose, CA (US); Steve Hsiung, Fremont, CA (US); Joe Luo, Cupertino, CA (US)

(73) Assignee: LSI Logic Corporation, Milpitas, CA (US)

( * ) Notice: Subject to any disclaimer, the term of this patent is extended or adjusted under 35 U.S.C. 154(b) by 0 days.

(21) Appl. No.: 10/289,074

(22) Filed: Nov. 6, 2002

(51) Int. Cl.$^7$ .............................................. G01R 31/02
(52) U.S. Cl. ..................... 324/765; 324/158.1
(58) Field of Search ................. 324/765, 754, 324/158.1, 750, 751, 752, 753; 250/269.1, 526; 365/600, 601, 606

(56) References Cited

U.S. PATENT DOCUMENTS

| | | | |
|---|---|---|---|
| 4,640,002 A | * | 2/1987 | Phillips et al. ................. 438/12 |
| 4,680,616 A | * | 7/1987 | Delahoy et al. ............... 257/62 |
| 4,811,081 A | | 3/1989 | Lyden |
| 5,051,738 A | * | 9/1991 | Tanielian et al. ............. 345/82 |
| 5,508,228 A | | 4/1996 | Nolan et al. |
| 5,543,724 A | | 8/1996 | Christopher |
| 5,545,465 A | | 8/1996 | Gaynes et al. |
| 5,611,884 A | | 3/1997 | Bearinger et al. |
| 6,043,670 A | | 3/2000 | Degani et al. |
| 6,288,559 B1 | | 9/2001 | Bernier et al. |
| 6,320,396 B1 | * | 11/2001 | Nikawa ...................... 324/751 |

* cited by examiner

Primary Examiner—David A. Zarneke
Assistant Examiner—Jimmy Nguyen
(74) Attorney, Agent, or Firm—Trexler, Bushnell, Giangiorgi, Blackstone & Marr, Ltd.

(57) ABSTRACT

A method for performing backside Photon Emission Microscopy (PEM) on wafer-level failure analysis. The method provides that a die is located by applying reversed-biased voltage to wafer and the backside of the wafer is thereafter observed. The die of interest will illuminate brightly, because of the electron-hole recombination from the reverse-biased protection diode. Such a method is easy to perform and provides a low cost and time-saving way to accurately identify a die and acquire emission.

12 Claims, 1 Drawing Sheet

DIE LOCATION ON UNGROUNDED WAFER FOR BACK-SIDE EMISSION MICROSCOPY

BACKGROUND

The present invention generally relates to methods of using an Infrared Emission Microscope (IREM) to analyze a die and specifically backside Photon Emissions Microscopy (backside PEM). The present invention more specifically relates to a new application of using an Infrared Emission Microscope (IREM) to perform wafer-level backside analysis.

Infrared Emission Microscopes (IREMs) have been used in the semiconductor industry to locate hot carrier emission and thermal emission sites in CMOS ICs (integrated circuits). They monitor visible and near-infrared photon emissions from ICs where they are powered up or exercised, for the purpose of locating and characterizing defects. The photons emitted from transistors, pn-junctions and other photon-generating structures are collected during analysis.

There are two major types of Photon Emission Microscopy (PEM): Frontside Photon Emission Microscopy that detects photon emerging from frontside of a die, and Backside Photon Emission Microscopy that detects photons passing through the silicon substrate and emerging from the backside of a die. With the ever-increasing number and density of metal layers in today's process technology, Frontside Photon Emission Microscopy as a fault location technique is being used less and less. Silicon allows the transmission of photons with energies less than its indirect bandgap energy (1.12 eV$\propto$1.107 $\mu$m wavelength for undoped silicon). By thinning heavily doped silicon substrates, and taking advantage of Silicon's transparency to certain $\lambda$, backside Photon Emission Microscopy is possible At the die level, backside Photon Emission Microscopy (PEM) is a straightforward procedure of biasing the device and collecting photons. At wafer-level, this task becomes complicated because there are the various dice on the reticle field and the numerous reticle fields on the wafer, and it is difficult to tell which die is the DUT (device under test) from the backside. A new method for die location must be provided before wafer-level Backside PEM can be performed. An aspect of the present invention provides such a method.

OBJECTS AND SUMMARY

A general object of an embodiment of the present invention is to provide a method for performing backside Photon Emission Microscopy (PEM) on wafer-level failure analysis.

Briefly, and in accordance with at least one of the foregoing objects, an embodiment of the present invention provides a method for performing backside Photon. Emission Microscopy (PEM) on wafer-level failure analysis, where the method provides that a die is located by applying reversed-biased voltage to the wafer and the backside of the wafer is observed. The die of interest will illuminate brightly, because of the electron-hole recombination from the reverse-biased protection diode. Such a method is easy to perform and provides a low cost and time-saving way to accurately identify a die and acquire emission.

BRIEF DESCRIPTION OF THE DRAWINGS

The organization and manner of the structure and operation of the invention, together with further objects and advantages thereof, may best be understood by reference to the following description, taken in connection with the accompanying drawing, wherein.

DESCRIPTION

Figure 1:
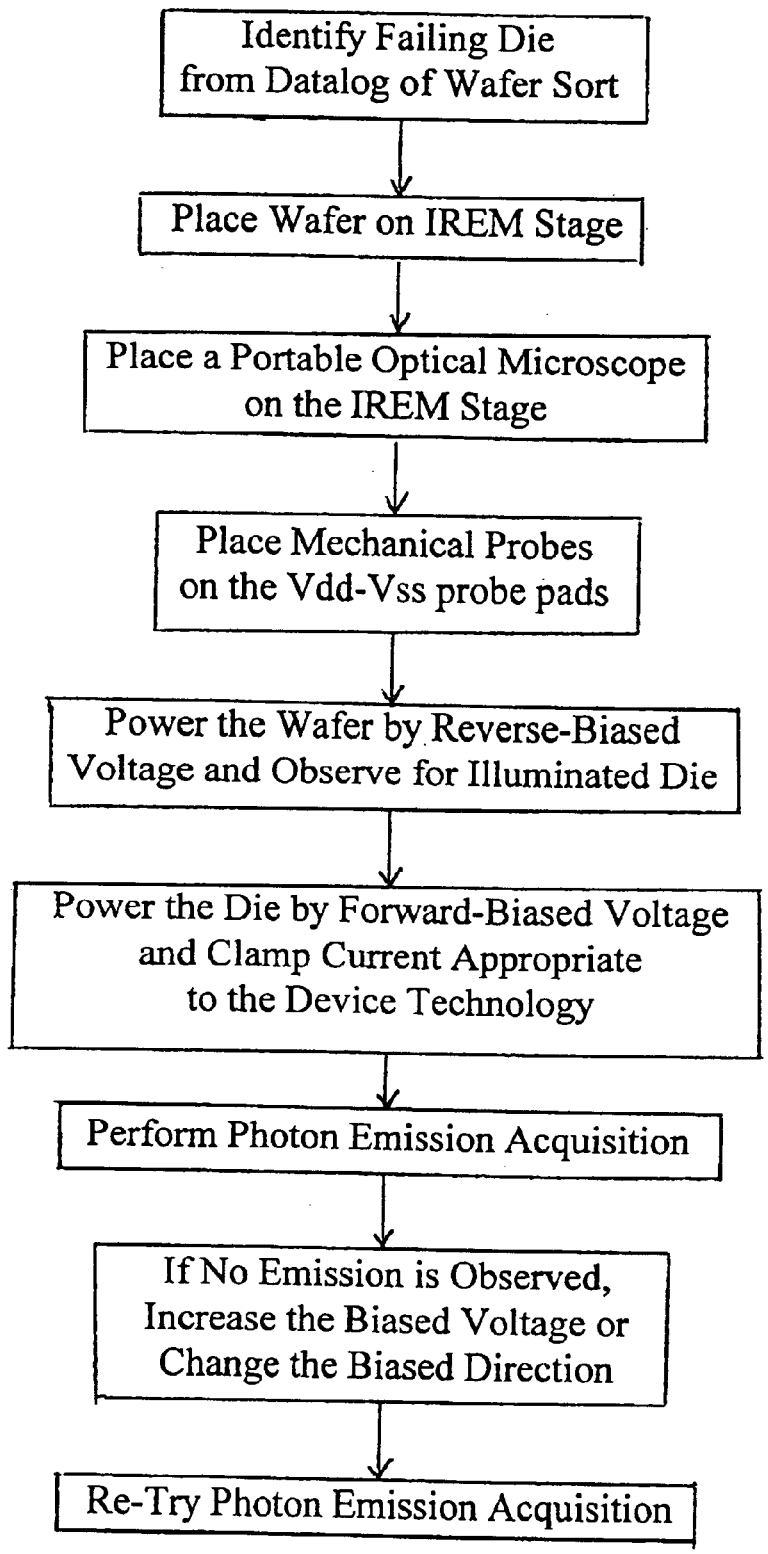
FIG. 1 is a flow chart illustrating a method for performing backside Photon Emission Microscopy (PEM) on wafer-level failure analysis, where the method is in accordance with an embodiment of the present invention.

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

As discussed above, at the die level, PEM is a straightforward task of biasing the device and collecting photons. But at wafer-level, this task is complicated because of the various dice on the reticle field, and the number of reticle fields on the wafer itself. To locate the die in a wafer before wafer-level Backside PEM can be performed is critical. An embodiment of the present invention provides a method for performing backside Photon Emission Microscopy (PEM) on wafer-level failure analysis, where the die is located by applying reversed-biased voltage to the wafer and then the wafer is observed. The die of interest will illuminate brightly, because of the electron-hole recombination from the reverse-biased protection diode.

FIG. 1 illustrates the method in more detail. As shown, first a failing die is identified from the datalog of wafer sort. Then, the wafer is placed on the IREM stage for backside Photon Emission Microscopy (PEM) analysis. Then, a portable optical microscope is placed on the IREM stage. Then, mechanical probes are placed on the Vdd-Vss probe pads, and the wafer is powered up by reverse-biased voltage. The die of interest should illuminate brightly, because of the electron-hole recombination from the reverse-biased protection diode. Once the die is found, the DUT (i.e., the die of interest) is powered up by forward-biased voltage and the current appropriate to the device technology is clamped. Then, photon emission acquisition is performed, such as for 20 seconds. If no emission is observed, the biased voltage is increased, or the biased direction is changed, and photon emission acquisition is re-tried.

Such a method of performing backside Photon Emission Microscopy (PEM) on wafer-level failure analysis is easy to perform and provides a low cost and time-saving way to accurately identify a die and acquire photon emission.

While an embodiment of the present invention is shown and described, it is envisioned that those skilled in the art may devise various modifications of the present invention without departing from the spirit and scope of the appended claims.

What is claimed is:

1. A method for performing backside Photon Emission Microscopy (PEM) on a wafer, said method comprising applying reversed-biased voltage to the wafer; observing the wafer to identify a die on the wafer which illuminates as a result of the reversed-biased voltage being applied; and after applying reverse-biased voltage to the wafer and observing the wafer to identify the die on the wafer which illuminates, powering up the die by forward-biased voltage.

2. A method as recited in claim 1, further comprising identifying a failing die from a datalog of sort.

3. A method as recited in claim 1, further comprising placing the wafer on an IREM stage and placing a portable optical microscope on the IREM stage.

4. A method as recited in claim 1, further comprising placing mechanical probes on Vdd-Vss probe pads on the wafer.

5. A method as recited in claim 4, further comprising clamping appropriate current while powering up the die by forward-biased voltage.

6. A method as recited in claim 4, further comprising acquiring photon emission while powering up the die by forward-biased voltage.

7. A method as recited in claim 6, further comprising increasing the biased voltage and re-acquiring photon emission.

8. A method as recited in claim 6, further comprising changing the biased direction and re-acquiring photon emission.

9. A method for performing backside Photon Emission Microscopy (PEM) on a wafer, said method comprising identifying a failing die from a datalog of wafer sort, placing the wafer on an IREM stage, placing a portable optical microscope on the IREM stage, placing mechanical probes on Vdd-Vss probe pads on the wafer, powering up the wafer by applying reversed-biased voltage to the wafer observing the wafer to identify a die on the wafer which illuminates as a result of the reversed-biased voltage being applied; and after applying reverse-biased voltage to the wafer and observing the wafer to identify the die on the wafer which illuminates, powering up the die by forward-biased voltage.

10. A method as recited in claim 9, further comprising clamping appropriate current, and acquiring photon emission while powering up the die by forward-biased voltage.

11. A method as recited in claim 10, further comprising increasing the biased voltage and re-acquiring photon emission.

12. A method as recited in claim 10, further comprising changing the biased direction and re-acquiring photon emission.

* * * * *